US010737119B2

(12) United States Patent
Arican et al.

(10) Patent No.: US 10,737,119 B2
(45) Date of Patent: Aug. 11, 2020

(54) APPARATUS AND METHOD FOR RADIATION THERAPY DEVICE COMMISSIONING AND QUALITY ASSURANCE

(71) Applicant: Ion Beam Applications S.A., Louvain-la-Neuve (BE)

(72) Inventors: Salih Arican, Poxdorft (DE); Christian Vogel, Postbauer-Heng (DE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 190 days.

(21) Appl. No.: 15/968,699

(22) Filed: May 1, 2018

(65) Prior Publication Data
US 2018/0318609 A1  Nov. 8, 2018

(30) Foreign Application Priority Data
May 2, 2017 (EP) .................................... 17169105

(51) Int. Cl.
*A61N 5/10* (2006.01)

(52) U.S. Cl.
CPC .... *A61N 5/1075* (2013.01); *A61N 2005/1074* (2013.01); *A61N 2005/1076* (2013.01)

(58) Field of Classification Search
CPC ............... A61N 5/1077; A61N 5/1075; A61N 2005/1076; A61N 2005/1074
See application file for complete search history.

(56) References Cited

U.S. PATENT DOCUMENTS 5,627,367 A    5/1997  Sofield
8,321,179 B2 * 11/2012  Simon ...................... A61N 5/10
                                                 250/252.1

(Continued)

FOREIGN PATENT DOCUMENTS

CN    105056407      11/2015
WO    WO-2011/011471   1/2011
WO    WO-2016/008901   1/2016

OTHER PUBLICATIONS

European Search Report issued in corresponding European Application No. 17 16 9105; 7 pages.

*Primary Examiner* — David P Porta
*Assistant Examiner* — Fani Boosalis
(74) *Attorney, Agent, or Firm* — Finnegan, Henderson, Farabow, Garrett & Dunner LLP

(57) ABSTRACT

This disclosure is related to an apparatus and method for commissioning or performing a quality assurance (QA) verification of a radiation therapy (RT) device. The device may comprise: (a) a motorised water phantom; (b) a RT controller configured for obtaining operation parameters of fields, and causing the RT device to emit a beam according to said operations parameters; (c) a QA controller having a memory for storing a measurements plan, the measurements plan including data defining a sequence of fields, and d) a reference radiation detector adapted and positioned for intercepting said radiation beam and for measuring the dose rate of said radiation beam. The reference radiation detector may be substantially transparent to the radiation beam. The QA controller may include an acquisition interface for acquiring and storing the dose rate from the reference radiation detector. The device may also include a processor configured to check the synchronism between the dose rate from the field radiation detector and the dose rate from the reference radiation detector.

16 Claims, 8 Drawing Sheets

(56) References Cited

U.S. PATENT DOCUMENTS

Figure 1:
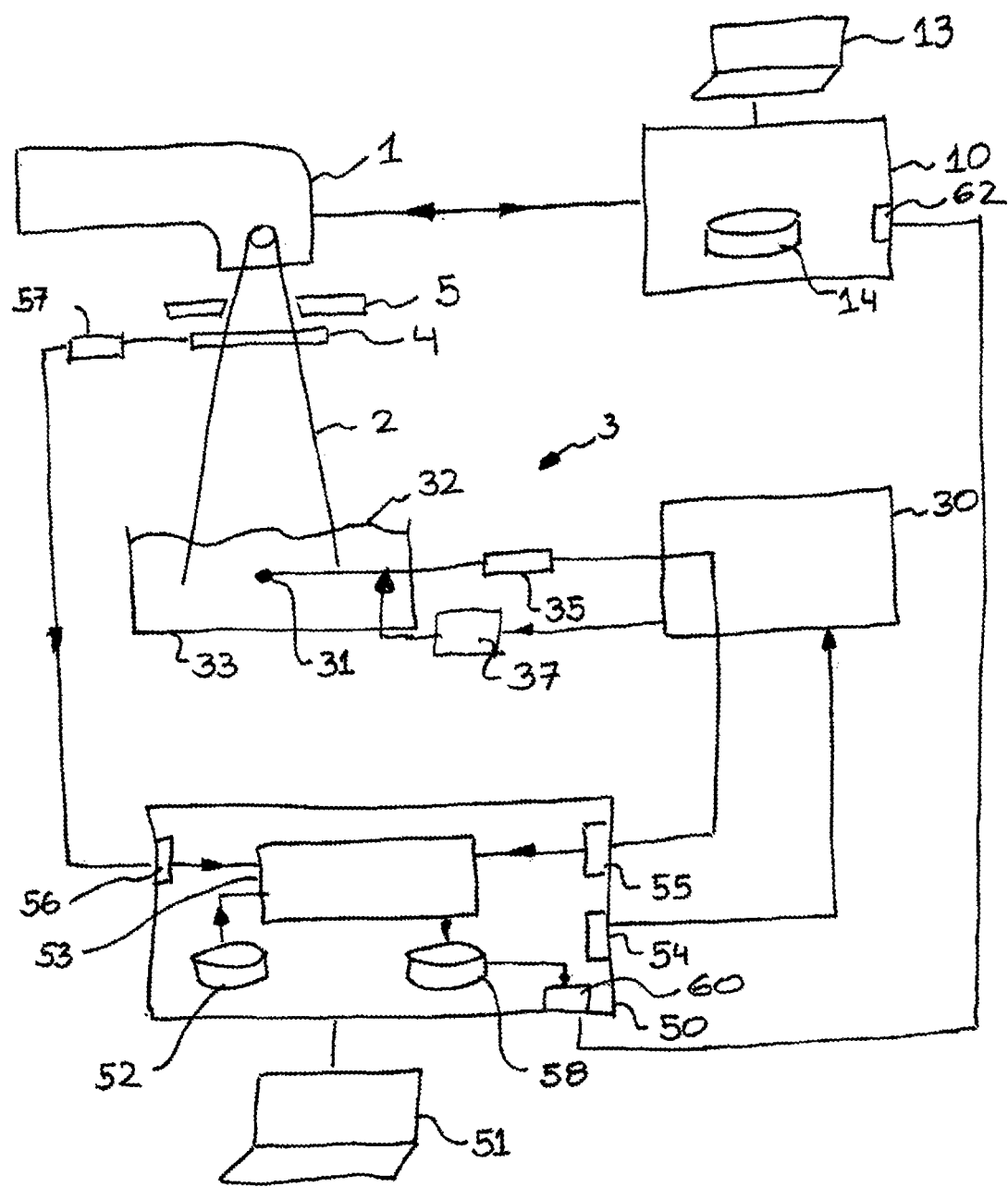

2010/0082294 A1  4/2010 Adnani
2015/0238778 A1  8/2015 Hildreth et al.

* cited by examiner

APPARATUS AND METHOD FOR RADIATION THERAPY DEVICE COMMISSIONING AND QUALITY ASSURANCE

CROSS-REFERENCE TO RELATED APPLICATIONS

This application claims the benefit of priority of European Patent Application 17169105.8, filed May 2, 2017, which is incorporated herein by reference in its entirety.

TECHNICAL FIELD

The present disclosure relates to radiation therapy equipment, and in particular, to an apparatus for commissioning or performing a periodic quality assurance verification of a radiation therapy device. The disclosure also relates to a method for commissioning or performing a periodic quality assurance verification of a radiation therapy device.

DESCRIPTION OF PRIOR ART

While delivering radiation to a patient as part of a treatment regime, accuracy is vital and a radio-therapeutic procedure must deliver the planned dose to eradicate a tumour while minimizing radiation exposure to healthy tissue. Delivering too much radiation may result in serious complications that could harm the patient, and delivering too little radiation will not destroy the malignant tissue.

Commissioning and (annual or periodic) quality assurance (QA) verification may be required to ensure that a radiation therapy (RT) device meets its specification, particularly, in terms of dose delivery, and to calibrate it. This step may be mandatory and required by medical standards. It is very important that any errors in the commissioning and QA verification are small.

One method known in the art for commissioning and periodic QA verifications of a RT device may comprise measurements of the spatial distribution of delivered dose with a field radiation detector positioned in a water phantom (WP) comprising a water tank. The beam may be directed into the water. A small-size field radiation detector such as diode or a small-size ionization chamber may be moved across the volume of the water tank, while measuring the dose.

The measurements may be done for a large number of different fields of the radiation beam and for a large number of positions of the field radiation detector in three dimensions, in the X, Y and Z directions. The field radiation detector may be moved in the water tank mechanically during individual scans, trajectories commonly parallel to the X, Y or Z axes.

Movements of the field radiation detector along a scan trajectory may require a certain time during which fluctuation of the output intensity of the RT device may occur. Measurements are therefore recorded relative to the signal of a reference radiation detector, which may be placed close to the edge of the radiation field to minimize perturbation of the radiation field.

One standard known commissioning or QA procedure may comprise the following steps:
A measurements plan is provided. The measurements plan comprises a sequence of fields, each field having a size and a shape such as a square, a beam energy, a dose rate and a dose. For each field, a set of scans is defined and may comprise horizontal scans across the field, at different depths in the water tank, and vertical scans, along an axis of the beam. The scans are either step-by-step scans and comprise a duration for staying at a set of positions, or continuous scan defined by continuous paths at a given speed, The measurements of the horizontal scans are used for determining transverse beam profiles. The vertical scans may be used for ascertaining percentage depth-dose (PDD) curves. In order to limit the time required for performing the test, a maximum field size may be selected among the field sizes of the measurements plan, according to the intended clinical use of the RT device.

For each field of the measurements plan:
the reference radiation detector is positioned close to the edge of the radiation field;
the RT device is configured for producing the required field;
the RT device is started for emitting a radiation beam towards the water tank;
simultaneously, the field radiation detector is moved according to the different scans of the field, and the signal measured by the field radiation detector is acquired. This acquisition is usually performed in continuous mode, i.e. the field radiation detector is automatically moved within the water tank, according to the scans, under control of a WP controller of a motorized water phantom and measurements of the accumulated dose are acquired after each of successive determined time intervals;
at the same time, the radiation beam is acquired with the reference radiation detector;
When the dose specified for the field is reached, the RT device automatically stops the beam. The detection of the dose may be performed by a monitor ionization chamber comprised in the RT device.

This procedure is repeated a large number of times for different radiation field sizes and may take several hours. It thus represents a non-negligible cost in term of human resources. To maximize the use of the RT device for treatment, the QA tests are often performed out of working hours (night, weekend). They may also be performed during normal working hours. In the latter case, the RT device cannot be used for treatment purpose and its availability for patient treatments is decreased.

This procedure is time consuming because the reference radiation detector has to be positioned manually by an operator repeatedly for each field. Proper verification requires discrete measurements at a large number of locations in the water tank. The operator also has to control both the RT device and the WP controller to set, deliver, and synchronously measure a large number of different fields. The probability occurrence of errors is also greatly increased because of the high number of human interventions during the time-consuming procedure. Thus, the quality of the scanned beam data is highly dependent upon the skill of the operator.

The operation of an RT device is controlled by an RT controller. The RT device may be controlled by an RT controller under different operation modes:
Semi-automatic mode: an operator uses an operator console of the RT controller for providing operation parameters such as field size and/or field shape, beam energy, dose rate, total dose, and for starting the beam. The beam is stopped when the total dose has been emitted. This process may be repeated for a sequence of fields.

Automatic mode: a file containing the operation parameters for a sequence of fields is provided to the RT controller. An operator initiates the operation and the RT controller directs the RT device to perform the sequence of operations. The file may be a DICOM-file.

A state of the art motorized water phantom such as the Blue Phantom obtainable from IBA dosimetry or such as described in PCT Pat. Publication WO2011/011471, allows automated positioning of the field radiation detector, but the operator should always manually position the reference radiation detector.

Therefore, a need remains for an apparatus and method for commissioning or performing a periodic quality assurance verification of a RT device allowing a faster and more reliable operation.

SUMMARY

The present disclosure is defined in the appended independent claims. Some embodiments are defined in the dependent claims. According to a first aspect, the present disclosure relates to an apparatus for commissioning or performing a quality assurance (QA) verification of a radiation therapy (RT) device able to emit a radiation beam, and that may comprise a beam limiting device adapted for limiting the radiation beam to a given field size and/or field shape, the apparatus may be comprising:
  a) a motorised water phantom (WP) comprising:
    a water tank;
    a field radiation detector configured for measuring a signal indicative of a field radiation dose rate of a radiation beam at a position (x, y, z) in said water tank;
    a mechanical drive configured for moving said field radiation detector to a given position (x, y, z) at a given speed in said water tank; and
    a WP controller configured for:
      instructing said mechanical drive to move the field radiation detector to said given position (x, y, z) at said given speed;
      acquiring a dose rate from said field radiation detector; and
  b) a RT controller configured for obtaining operation parameters of fields comprising a field size and/or field shape, a beam energy, a dose rate and a dose, and causing the RT device to emit a beam according to said operations parameters.
The apparatus further may comprise
  c) a QA controller that may comprise
    a memory storing a measurements plan, said measurements plan comprising data defining a sequence of fields, each field having a size and a shape, a beam energy, a dose rate and a dose, each field comprising a set of scans each scan defining a path to be measured in the radiation beam;
    a communication interface for transferring the data of said scans to said WP controller;
    an acquisition interface for acquiring and storing the dose rate from said field radiation detector;
  d) a reference radiation detector adapted and positioned for intercepting said radiation beam and for measuring the dose rate of said radiation beam, said reference radiation detector being substantially transparent to said radiation beam.
The QA controller may comprise an acquisition interface for acquiring and storing the dose rate from said reference radiation detector, and a processor adapted for checking the synchronism between the dose rate from the field radiation detector and the dose rate from the reference radiation detector.

The measured dose rate from the field radiation detector may correspond to the irradiation of the field.

In a semi-automatic embodiment of the apparatus according to the disclosure, the QA controller may comprise a QA operator console adapted for displaying the data of said sequence of fields, and the RT controller may comprise a RT operator console comprising means for inputting the data of a selected one of said fields, and for starting the beam.

In an automatic apparatus embodiment of the apparatus according to the disclosure, the QA controller may comprise a processor for producing a file containing data for a sequence of fields, and a communication interface for transferring said file to said RT controller, the RT controller comprising a communication interface for receiving said file and starting the execution of the fields contained therein.

In one embodiment of the apparatus, the field radiation detector may comprise a first electrometer, and/or the reference radiation detector may comprise a second electrometer, and the WP controller and/or the QA controller may respectively be configured for automatically adjusting the gain of the first electrometer and/or of the second electrometer as a function of a maximum dose rate of a field.

The field radiation detector may be selected from the group consisting of a scintillating detector, a diode, a linear array of diodes, a 2D planar array of diodes, an ionisation chamber, a linear array of ionisation chambers, and a 2D planar array of ionisation chambers.

The reference radiation detector may be an integral ionisation chamber, wherein said integral ionisation chamber may be configured for intercepting at least 90% of the field region of the radiation beam, preferably 95%, more preferably the whole field region of the radiation beam, the field region defined as the separation between the 50% dose level points on the beam profile and a penumbra around the central region.

The RT controller may be configured for generating a log file comprising at least one of the following information: a count of monitor units (MU) emitted by the RT device, the presence or not of a beam limiting device, the presence or not of a multileaf collimator, a sequence of records, comprising at least one of: the position of the leaves of the multileaf collimator, the orientation of the beam, one or more characteristic of the beams; and the QA controller may further use the log file for checking the synchronism between the sequence of radiation beams and the sequence of scans.

The QA controller may be configured for checking the synchronism between the sequence of radiation beams and the sequence of positions by at least one of the following means:
  a) determining the presence or the absence of detection of the radiation beam with the reference radiation detector;
  b) comparing the value of the signal measured with the reference radiation detector with a field size defined in the measurements plan;
  c) comparing the sequence of radiation beams and their characteristics with the content of a log file comprising records of RT device operational data, the apparatus being an apparatus wherein the RT controller is configured for generating a log file.

According to a second aspect, the present disclosure relates to a method for commissioning or performing a periodic quality assurance verification of an RT device which may be comprising the following steps:
  a) one provides an apparatus according to the disclosure;
  b) one obtains a measurements plan comprising a sequence of fields, each field comprising a set of scans;
  c) one provides said sequence of fields to the RT controller;
  d) one provides the set of scans to the WP controller;
  e) one causes the RT controller to control the RT device for emitting said fields;
  f) when the QA controller receives a signal from the reference radiation detector that a beam was started, the QA controller instructs the WP controller to start moving the field radiation detector according to the scans;
  g) the QA controller acquires the measurements from the field radiation detector and from the reference radiation detector;
  h) The QA controller checks the synchronism between the measurements acquired from the field radiation detector and the measurements acquired from the reference radiation detector.

In a semi-automatic embodiment of the method,
the apparatus may be an apparatus according to a semi-automatic embodiment of the disclosure;
step b) may be performed by viewing the data of the fields of the measurements plan displayed at an operator console of the QA controller;
step c) may be performed by entering the data of the fields of the measurements plan to the RT controller by using an operator console of the RT controller.

In an automatic embodiment of the method,
the apparatus may be an apparatus according to an automatic embodiment of the disclosure;
step b) may be performed by the QA controller producing a file containing the sequence of fields
and step c) may be performed by the QA controller providing said file to the RT controller.

In an embodiment of the method, the check of the synchronism between the sequence of fields and the set of scans with the QA controller may be determined according to at least one of:
  a) the presence or the absence of detection of the radiation beam with the reference radiation detector;
  b) the comparison of the value of the signal measured with the reference radiation detector with a field size defined in the Measurements plan;
  c) comparing the sequence of radiation beams and their characteristics with the content of a log file comprising records of RT device operational data, the apparatus being an apparatus wherein the RT controller is configured for generating a log file.

The method may comprise the step of emitting a warning notification with the QA controller if the sequence of radiation beams and the sequence of positions lose synchronism.

The method may further comprise one of the following steps of:
  temporary suspending the sequence of radiation beams or the sequence of positions;
  restarting sequence of radiation beams and the sequence of positions from the beginning or from the last emission and movement that were synchronous.

When the apparatus is an apparatus comprising a first and/or a second electrometer, the method may further comprise at least one of the steps of:
  (A) automatically adjusting the gain of the field electrometer as a function of a maximum dose rate of each beam of the sequence of radiation beams;
  (B) automatically adjusting the gain of the reference electrometer as a function of a flux rate of each beam of the sequence of radiation beams According to a third aspect, the present disclosure relates to a computer program comprising instructions which, when the program is executed by a computer, cause the computer to carry out at least one of the steps (b) to (h) of the automatic embodiment of the method.

According to a fourth and last aspect, the present disclosure relates to a computer-readable medium having stored thereon the computer program of the third aspect of the disclosure.

SHORT DESCRIPTION OF THE DRAWINGS

These and further aspects of the disclosure will be explained in greater detail by way of example and with reference to the accompanying drawings.

FIG. 1 illustrates an example of apparatus for commissioning or performing a periodic quality assurance verification of a RT device according to the disclosure, in relation to a RT device.

FIGS. 2(a) to (e) schematically depict several examples of radiation fields and measurement points, for use in methods according to the disclosure.

Figure 3:
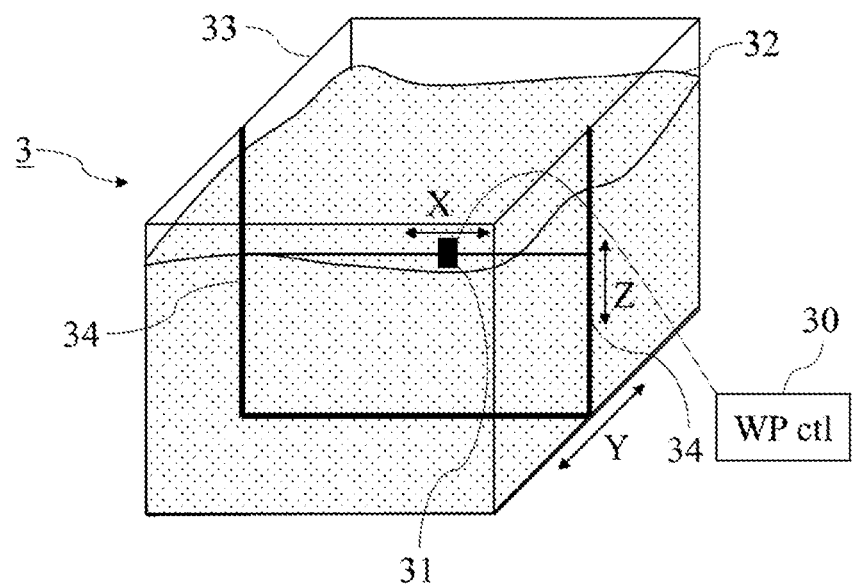

FIG. 3 depicts a schematic example of a motorized water phantom for use in an apparatus and method of the disclosure.

FIGS. 4(a) to (e) illustrate examples of commissioning or QA verifications in which the predefined sequences of radiation beams and predefined the sequences (measurements) are synchronous (a) or not (b) to (e) to each other.

Figure 5:
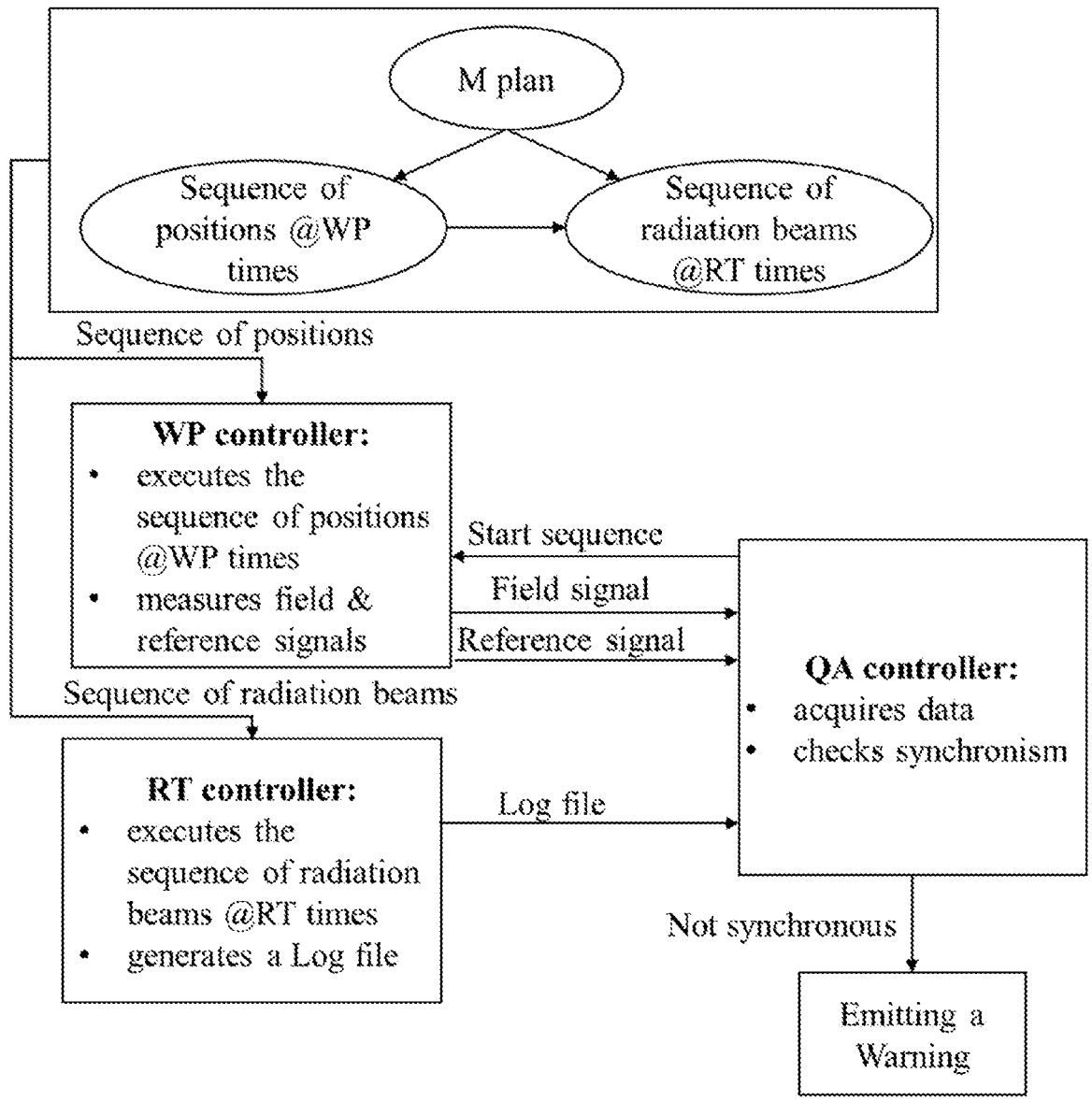

FIG. 5 illustrates a diagram of a commissioning or QA verification.

The figures are not drawn to scale.

DETAILED DESCRIPTION

FIG. 1 illustrates one preferred embodiment of an apparatus according to the present disclosure, for commissioning or performing a periodic quality assurance (QA) verification of a radiation therapy (RT) device 1 able to emit a radiation beam 2 and comprising a beam limiting device 5. The apparatus comprises:
  a) a motorised water phantom 3;
  b) an RT controller 10;
  c) a reference radiation detector 4
  d) a QA controller 50.

The motorised water phantom 3 may comprise:
  a water tank 33;
  a mechanical drive 37 for moving the field radiation detector to a position in the water tank;
  a field radiation detector 31 configured for measuring a signal indicative of a field radiation dose rate of the radiation beam 2 at least one position in the water tank;
  a WP controller 30 configured for:
    instructing the mechanical drive to move the field radiation detector to a given position (x, y, z) in the water tank; and
    acquiring a dose rate from the field radiation detector.
  optionally, an electrometer 35 for amplifying and shaping the signal acquired from the field radiation detector. The electrometer may have a variable gain that may be adjusted by the WP controller.

The motorised water phantom may operate in two operating modes: the step-by-step mode or the continuous mode.

In step-by-step mode, the field radiation detector is moved successively to a predefined set of positions, staying at a position for a controlled time, and moved to a subsequent position in a controlled time. The field radiation detector is stopped at each position of the predefined sequence of positions for a given time required for the measurement.

In continuous mode, the field radiation detector is moved along a predetermined track, according to a predetermined speed. Contrary to the step-by-step mode, the signal indicative of the dose rate is acquired during uninterrupted movement of the field radiation detector. Then the WP controller 30 (or any other suitable controller) converts the signal acquired in a dose distribution. For example, it computes the integral of the signal over a time necessary to travel a given distance. The computed integrals of the signal (integrated values) are indicative of the dose at a given set of discrete measurement points.

The RT controller 10 provides operation parameters to the RT device and instructs the RT device to start the beam. In a semi-automatic embodiment of the disclosure, the RT controller comprises an RT operator console 13. An operator may then enter the operation parameters and start the beam. In an automatic embodiment of the disclosure, the RT controller is configured for receiving a file containing the sequence of fields to be emitted. The RT controller then starts emitting this sequence of fields. An embodiment of the disclosure may comprise both the features for semi-automatic and automatic modes, and operate under both modes as required by the operator. The RT controller may comprise a log file 12 wherein operation parameters of the RT device are stored.

The reference radiation detector 4 is located between the beam limiting device 5 of the RT device, and the water tank 33 of the water phantom 3 and is configured for measuring a signal indicative of the integrated radiation fluence of the reference radiation beam. The time resolved measurements of the radiation fluence rate ($J/m^2/s$) integrated over the area of the reference radiation beam is the flux rate (J/s). The signal is generated from a volume traversed by the radiation beam of the reference radiation detector. The surface has a size sufficient for being traversed by at least 90% of the central region of the radiation beam, preferably 95%, more preferably the whole central region of the radiation beam when positioned in said radiation beam. For example, the reference radiation detector is large enough to measure large radiation field (10 cm×10 cm at isocentre) or small radiation field (less than 4 cm×4 cm at isocentre). The reference radiation detector is preferably located between the exit of the RT device (where the radiation beam is emitted) and the water surface, and provides a reproducible measurement, independent of other operating conditions of the apparatus. For example, a suitable reference radiation detector includes the circular (round Stealth chamber) or square (square Stealth chamber) ionization chamber provided by the applicant. The circular chamber has a sensitive region having a diameter of 92 mm. The square version has a sensitive area of 220 mm×220 mm, and a sensitive volume of 580 $cm^3$ (See for example the international application WO2016/008901 for an extensive description, the document is enclosed by reference). Optionally, an electrometer 57 for amplifying and shaping the signal acquired from the reference radiation detector may be provided. The electrometer 57 may have a variable gain that may be adjusted by the QA controller.

The QA controller 50 manages the operations of commissioning or performing periodic QA. It comprises a processor 53, and a memory 52. The memory may contain a measurements plan designed for verifying the RT device. The measurements plan comprises a sequence of fields, each field having a size and a shape such as a square, beam energy, a dose rate and a dose. For each field, a set of scans is defined and may comprise horizontal scans across the field, at different depths in the water tank, and vertical scans, along an axis of the beam. The measurements plan may be adapted according to the needs, e.g. a measurements plan for commissioning may be more extensive than a measurements plan used for periodic QA. E.g., a measurements plan for an RT device used only for small fields, may comprise only the smaller fields and be less time-consuming. The QA controller comprises a communication interface 54 for transferring the scans data to the WP controller 30. The QA controller comprises an acquisition interface 55 for acquiring dose rates from the field radiation detector 31, either directly, or, as represented on FIG. 1, through the WP controller 30. The QA controller also comprises an acquisition interface 56 for acquiring dose rates from the reference radiation detector 4. In a semi-automatic embodiment of the disclosure, the QA controller comprises a QA operator console 51. The fields of the measurements plan are displayed at this operator console. The operator may then read them and enter them at the operator console 13 of the RT controller 10. In an automatic embodiment of the disclosure, the QA controller is configured for producing a file 58 containing all fields from the measurements plan, adapted for being executed by the RT controller. This file is transferred through the communication interface 60 and received by the RT controller through communication interface 62.

The apparatus according to the present disclosure enables or is otherwise configured to allow optimization of the commissioning procedure and the periodic QA verification. The commissioning or periodic QA verification may be improved by using the reference radiation detector 4 and the QA controller 50. This improves the efficiency of measurements with the motorized water phantom 3 and reduces the intervention of the operator. The motorized water phantom enables automatic and precise positioning of the field radiation detector 31. The intervention of the operator is reduced due to several factors, including, for example:

The automated movement of the field radiation detector;

The reference radiation detector, which is substantially transparent to the radiation beam and located between the RT device and the motorised water phantom, does not need to be repositioned at each field size change; In particular, the operator does not need to enter the treatment room to carry out this task.

In the embodiment of the automatic mode, the sequence of radiation fields and the sequence of positions are executed automatically; the automation of the movements of the field radiation detector and the non-stopping of the RT device to enter the room also allow reducing the time of the commissioning or periodic QA verification; and The QA controller 50 is configured for checking the synchronism between the sequence of radiation beams and the sequence of positions.

The quality of the measurement is thus not compromised by fatigue of the operator and the risk of human errors is greatly decreased.

The RT device 1 may comprise one of the following: a gamma source, a cyclotron, a synchro-cyclotron, a synchrotron, or a linear accelerator (LINAC). Preferably, the RT device comprises a LINAC. For example, LINACs may generate high energy electron beams. These electron beams may be used directly for radiation therapy or may interact with a target and generate X-rays (photons) that are used for radiation therapy.

The RT device 1 may be configured to emit a radiation beam. The radiation beam, according to contemplated embodiments, may comprise at least one of the following: a beam of photons (X-ray or γ), electrons, protons or ions. Preferably, the radiation beam may be a beam of photons. The RT device may comprise a head fixed on a gantry; the gantry may be configured to orientate the beam. Preferably, the beam is orientated vertically towards the motorized water phantom 3 and, more preferably, the beam is arranged normal (perpendicular) to a water surface 32 of the motorized water phantom. A radiation beam may have a beam profile composed of a field region, a penumbra and an out of field region. The field region represents the central portion of the profile extending from a beam central axis to within about 1-1.5 cm from the geometric field edges of the beam. The geometric field size, indicated by the optical light field, may be defined as the separation between the 50%-dose-level points on the beam profile. The out of field region is the region outside the radiation field. The dose in this region is low. The penumbra is the region comprised between the central region and the penumbra. In this region, the dose profile decreases rapidly.

The RT controller 10 may generate a log file 12 comprising at least one of the following set of information: a timestamp, a count of beams emitted by the RT device, the presence (or the lack of presence) of a multileaf collimator or other beam-delimiting devices, a sequence of records comprising at least one of: a timestamp, the position of the leaves of the multileaf collimator and other beam limiting devices, the orientation of the beam, one or more characteristic of the beams (for example their intensity). The log file is, thus, a file comprising information on the states of the RT device 1 during its use. According to a preferred embodiment of the disclosure, a log file is used for improving the computation and reliability of the check of the synchronism between the sequence of radiation beams and the sequence of positions. The RT controller may be configured to send the log file 12 to the QA controller 50.

The commissioning or the QA verification of a RT device 1 may be initiated by an operator who may define or select a measurements plan. The measurements plan may comprise, for example, several radiation fields (geometry of the emitted beam), several beam qualities (types of radiation), the number of monitor units (MU) or dose corresponding to the amount of radiation to be delivered and the intensity (MU/minute) or dose rate of the radiation beam 2 that are determined to test the conformity of the RT device. The operation may be performed under two operation modes: a semi-automatic mode and an automatic mode.

Semi-Automatic Mode

In the semi-automatic mode, the procedure for performing commissioning or a periodic quality assurance verification of a RT device may comprise the following steps:

1. A measurements plan as described above at paragraph [0008] is provided to a QA controller. The data of the fields of the measurements plan are displayed at an operator console of the QA controller. A reference radiation detector having a size suitable for measuring the largest field of the measurements plan may be positioned between the beam limiting device 5 of the RT device, and the water tank 33.
2. For each field of the measurements plan:
   a. The QA controller or the operator may provide the set of scans for the field to the WP controller;
   b. The operator may configure the RT device according to said field using an operator console of the RT controller and starts the RT device for producing a radiation beam, until the given dose or number of monitor units is produced;
   c. When the QA controller receives a signal from the reference radiation detector that a beam was started, the QA controller may instruct the WP controller to start moving the field radiation detector according to the set of scans;
   d. The QA controller may acquire the measurements from the field radiation detector and from the reference radiation detector;
   e. The QA controller may check the synchronism between the irradiation of the field and the set of scans by checking that
      1) The measurements of the reference radiation detector correspond to the intensity expected from the size of the field; and
      2) The expected number of measurements of the field radiation detector occurred during irradiation of the field.

Automatic Mode

In the automatic mode, the procedure for performing commissioning or a periodic quality assurance verification of a RT device may comprise the steps of:

1. A measurements plan as described above at paragraph [0008] is provided to a QA controller. Based on this measurements plan, the QA controller produces a file containing the sequence of fields. This file may be under the form of a DICOM file. The file is provided to the RT controller. A reference radiation detector having a size suitable for measuring the largest field of the measurements plan may be positioned between the beam limiting device 5 of the RT device, and the water tank 33. The RT controller may start executing the sequence of fields.
2. For each field of the measurements plan:
   a. The QA controller may provide a set of scans for the next field to be irradiated to the WP controller.
   b. The RT controller may start the beam for the field;
   c. When the QA controller receives a signal from the reference radiation detector that a beam was started, the QA controller may instruct the WP controller to start moving the field radiation detector according to the set of scans.
   d. The QA controller may acquire the measurements from the field radiation detector and from the reference radiation detector;
   e. The QA controller may check the synchronism between the irradiation of the field and the set of scans by checking that
      i. The measurements of the reference radiation detector correspond to the intensity expected from the size of the field; and
      ii. The expected number of measurements of the field radiation detector occurred during irradiation of the field.

It is not possible to directly instruct the RT device to deliver a radiation beam for a given time. The RT controller may be configured to instruct the RT device to deliver a given number of MU. The dose rate, dr, (MU/min) delivered by the RT device is provided by the manufacturer of the RT device and is known within a given margin. From that, the time, T, for delivering a given number of MU is computed and is equal to $T=MU/dr$. This time T has to be related to the time spent by the motorized water phantom 3 for executing the predefined sequence of positions, at predefined WP times. For example, if the time spent by the motorized water phantom 3 for executing the predefined sequence of positions is equal to 30 s, and the dose rate is R=450 (MU/min), the radiation beam has to deliver at least 0.5 min·450 MU/min=225 MU.

The dose rate of a RT device is not very stable in the long term. The dose rate may change on a daily scale. For example, a planned dose rate of 300 MU/min may lead to a delivered dose rate of 280 MU/min. In one embodiment, the QA controller is thus configured for performing a preliminary measurement (reference and field at a fixed position) with a given field size, to calibrate the sensitivity of the detectors (e.g. C/MU) and to determine the effective dose rate (MU/min). For example, 100 MU with a field of 10×10 cm² and a dose rate of 500 MU/min may be delivered. Signals are measured with field radiation detector (at a reference position in water, e.g. at isocenter) and with the reference detector. From any of these signals measured, the actual dose rate is computed.

Figure 2:
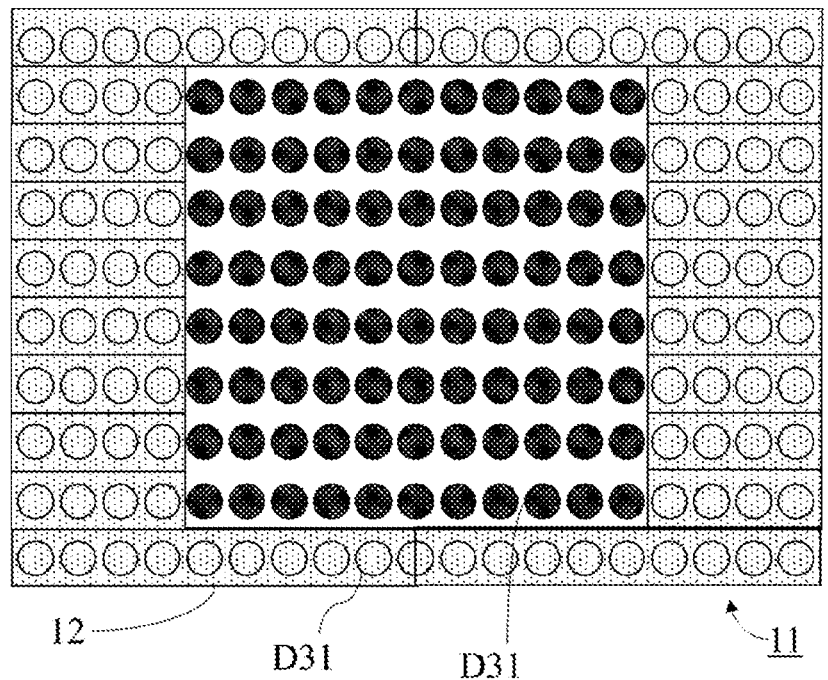
Figure 2B:
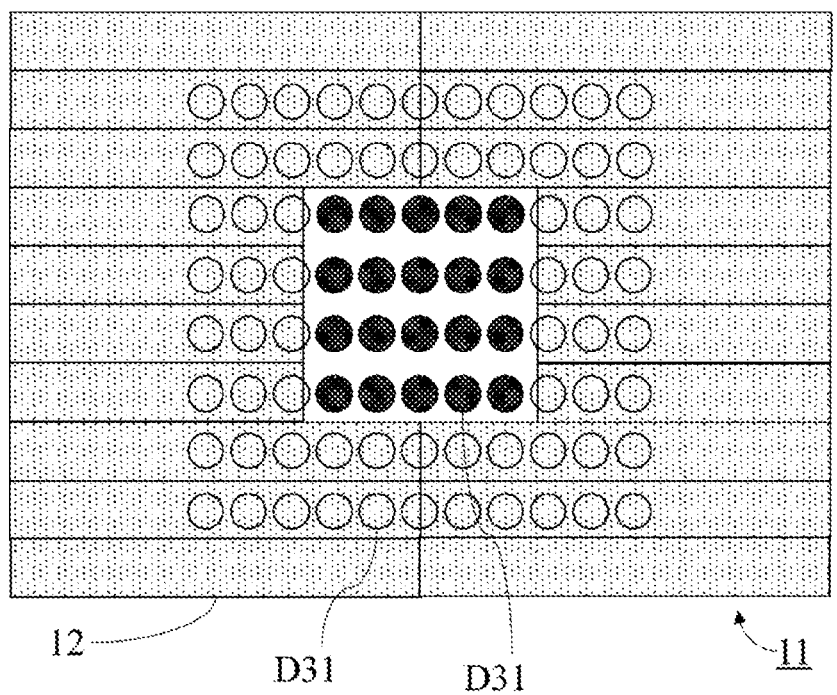
Figure 2C:
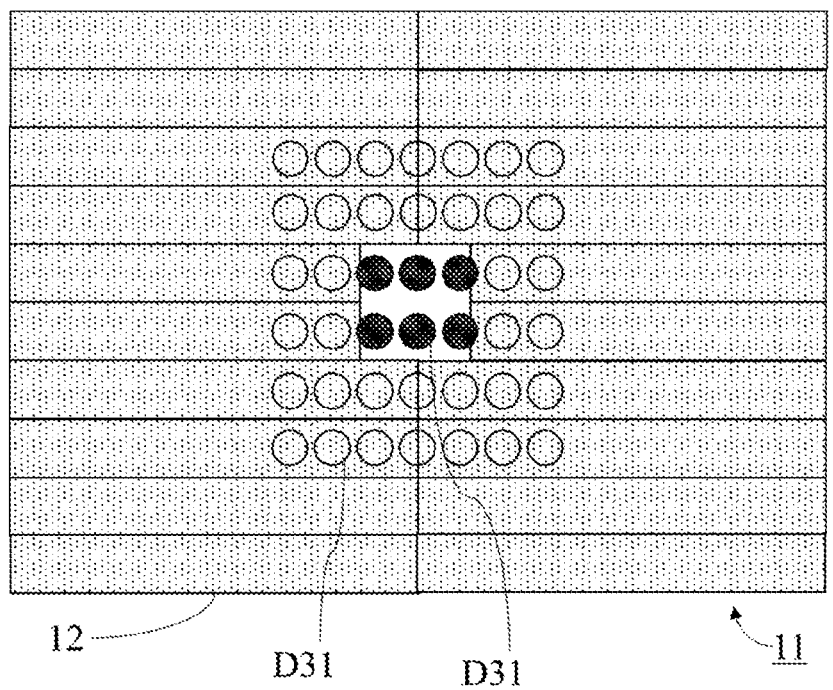
Figure 2D:
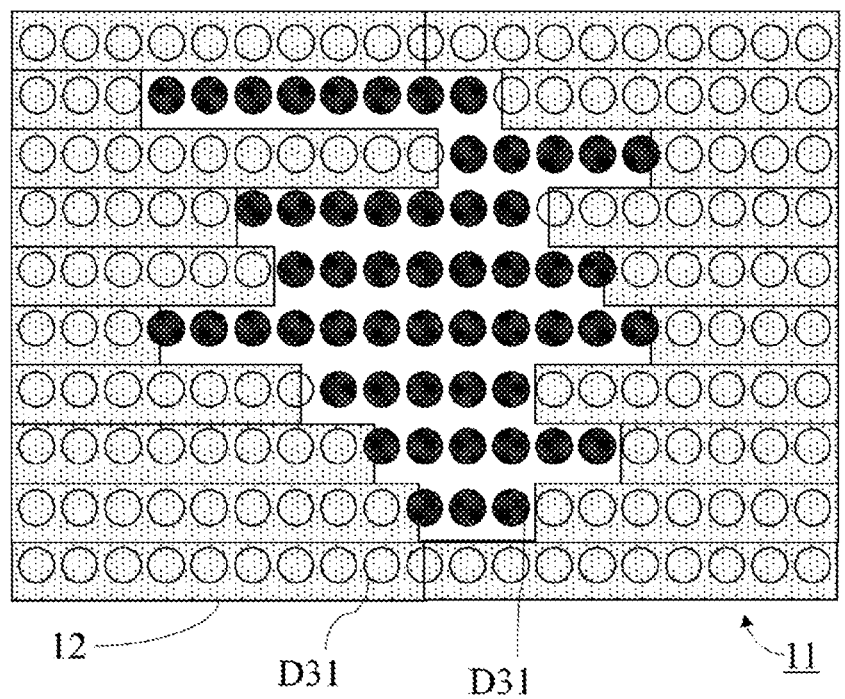

The RT device 1, in at least one embodiment, comprises a beam limiting device 5 such as a collimator or a multileaf collimator (MLC). FIG. 2 shows some examples of MLCs in different configurations. An MLC is an apparatus comprising a plurality of individual "leaves" 12 of a high atomic numbered material (for example tungsten). The individual leaves may move independently in a direction normal to the radiation beam such that leaves are in and out of the path of the radiation beam. Leaves that are within the path of the radiation beam block it thus allowing shaping of the radiation beam conformal to the intended target (e.g. a tumor). Specifically, conformal radiation therapy and Intensity Modulated Radiation Therapy (IMRT) may be delivered using MLC's.

The beam limiting device 5 allows defining size and shape of radiation fields. For example, the field of radiation may be rectilinear, for example a square of 40 mm×40 mm at isocentre of the RT device when the leaves are fully opened (FIG. 2(a)). The size of the square may be reduced to smaller dimension such as illustrated on FIGS. 2(b) and (c) and may be, for example reduced to 3 mm×3 mm. The shape of the field may depend on the shape of a (virtual) treatment area, for example a (virtual) tumour (see FIG. 2(d)). During a commissioning or a QA verification, several fields may be established as part of the Measurements plan and are tested sequentially in order to test the RT device 1.

In one embodiment, the QA controller may be configured for optimising the measurements plan. For example, the change of the size and/or shape of the field require modifying the positions of the leaves of a MLC. This operation takes some time. It is thus more efficient to perform all the measurements with a given field size consecutively. The QA controller thus preferably checks the measurements plan before computing the predefined sequence of positions and the predefined sequence of radiation beams and proposes an optimization to the user.

FIG. 3 illustrates an example of a motorized water phantom 3 for use in an embodiment of the present disclosure. A motorized water phantom comprises a water tank 33 that is filled with water to a top level, this top level defining a water surface 32. The water tank may comprise a mechanical drive for moving the field radiation detector and comprising arms 34 supporting a field radiation detector 31. The arms and the field radiation detector move along three orthogonal axes X, Y, and Z thus enabling the field radiation detector to reach a volume of measurement points within the water tank. Motors move the arms and the field radiation detector automatically according to at least one predetermined sequence and, preferably, according to any one of a plurality of predetermined sequences.

Commissioning or QA verification may be performed faster in continuous mode. The motorised WP 3 thus preferably operates in continuous mode. In FIGS. 2(a) to (e), the circles represent either the computed values of the dose rate obtained in continuous mode or the measured values of the dose rate obtained in step-by-step mode. In the next, these circles will be referred to points of measurement independently of the operating mode of the motorised WP.

In one embodiment, the motorized water phantom may comprise position sensors that are used to accurately verify the position of the field radiation detector. For example, the position of the field radiation detector may be determined with an accuracy better than 0.5 mm, preferably better than 0.1 mm. The WP controller 30 may then be configured for checking the position of the field radiation detector with the information coming from the position sensors of the motorized water phantom 3. For example, the motorized water phantom may be a Blue Phantom² brand water phantom of the applicant.

The field radiation detector 31 of the motorized water phantom 3, in one contemplated embodiment comprises any at least one of the following: a diode, a linear array of diodes, a 2D planar array of diodes, an ionisation chamber, a linear array of ionisation chambers, or a 2D planar array of ionisation chambers, a scintillating detector. The field radiation detector may measure a signal indicative of a field radiation dose rate of the radiation beam 2 at a given position or at given positions in the motorized water phantom. For example, the smallest ionization chambers provided by the applicant respectively having an active volume of 0.01 cm³ and 0.04 cm³, an inner radius of 1 and 2 mm and a sensitivity of 94·10⁷ (Gy/C) and 317·10⁷ (Gy/C). In another example, diodes are used such as the RAZOR Diode Detector-brand diode (available from the applicant). This diode has a diameter of the active area of substantially about 0.6 mm, a thickness of the active volume of substantially about 0.02 mm, and a sensitivity of substantially about 4.1 (nC/Gy). Preferably, the field radiation detectors according to the disclosure have an active area equal or smaller than 0.5 cm², more preferably equal or smaller than 0,3 cm². FIG. 2 illustrates some examples of field dose measurements D31 at different points of measurement for different radiation fields.

The reference radiation detector 4 may be substantially transparent to the radiation beam and located between the RT device 1 and the motorised WP 3. The terms "substantially transparent" correspond to a transmission of at least 95% of the radiation beam intensity, preferably at least 97%, more preferably at least 99%. In other words, the attenuation of the radiation beam is less than 5%, preferably less than 3%, more preferably, less than 1%.

The reference radiation detector 4, in one embodiment according to the present disclosure comprises a transmission ionization chamber detector having an attenuation equivalent to less than 1 mm Al or even preferably less than 0,5 mm Al.

The field radiation detector 31 and the reference radiation detector 4 may comprise a first electrometer 35 and second electrometer 57 respectively. In the context of this document, an electrometer is an electrical instrument for measuring electric charge or current produced by a radiation detector (ionization chamber or diode). The current measured with the first electrometer 35 is proportional to the size of a radiation field. For example, the signal changes of a factor 400 when varying the field size from 2×2 cm² to 40×40 cm². The maximum current measured with the field electrometer changes with depth, Z, and field size according to a function which is well known by the skilled person. For example, the signal (at the centre of the fields) changes of a factor 2 (called "output factor" in radiotherapy dosimetry) when varying the field size from 2×2 cm² to 40×40 cm². These variations may lead to overshoot of the measurements. It is thus important to correctly set the gain of the electrometers to ensure proper measurements. The electrometers allow the WP controller 30 and the QA controller 50 to automatically adjust the gain of the field electrometer as a function of a maximum dose rate of each field of the sequence of radiation fields and for automatically adjusting the gain of the second electrometer 57 as a function of a maximum flux rate and size of each beam of the sequence of radiation beams. Preferably, a reference measurement is performed to determine the correct gains of the field and reference electrometers.

The QA controller 50 is configured for acquiring field radiation dose rate and flux rate, and, based on these doses, for checking the synchronism between the sequence of radiation beams and the sequence of positions. For example, this check may be done by determining the presence or the absence of detection of the radiation beam with the reference radiation detector.

FIG. 5 illustrates a diagram of the automated commissioning or QA verification according to the disclosure. A measurements plan may first be established to test the RT device 1 and thus to check its conformity to its theoretical characteristics. The gantry of the RT device 1 is usually set to 0° angle for the commissioning or QA verification. The measurements plan may comprise the definition of at least one of:

several radiation fields, Fi with i=1 to kf, such as squared radiation fields (FIGS. 2(*a*) to (*c*)) or more complex shapes (FIGS. 2(*d*) and (*e*)), including (virtual) treatment area;

a sequence of positions, Pij with j=1 to kp, in the motorised WP; as described above, the sequence may be a discrete sequence in step-by-step mode or a continuous sequence in continuous mode;

several beam qualities, for example 4, 5 and 6 MV;

duration of the scan;

dose rate of the radiation beam;

number of MU to be delivered by the radiation beam.

The sequence of positions in the motorised WP, at different (pre)determined WP times may be transmitted to the WP controller. The number of positions likely depends on the size of the radiation field. The sequence of positions corresponds to points in the X, Y, and Z directions in the motorised WP. The X and Y directions correspond to the plane normal to the radiation beam in the motorised WP, and the direction Z (depth) correspond to the direction parallel to the radiation beam. For each radiation field, a sequence of positions is established in the X, Y plane for several depths, Z, and possibly for several beam qualities. The sequence of positions in the X, Y plane may cover the whole plane or only a fraction of the plane, for example a cross line along the X and Y directions and a cross line along the diagonals such as illustrated on FIG. 2(*e*).

The signal of the radiation beam 2 may be measured with the field radiation detector at these points of measurements (corresponding to either the computed values of the dose rate obtained in continuous mode or the measured values of the dose rate obtained in step-by-step mode). The points of measurements are illustrated on FIG. 2 by circles. Empty circles represent the points of measurements for which the dose is not significant (nearly equal to 0) and the filled circles represent the points of measurements for which a significant dose is measured. The WP controller 30 may be configured to automatically instruct the motorized water phantom 3 to move the field radiation detector 31 along a predetermined track. The movement is alternatively, sequential (step-by-step mode) or continuous (continuous mode). For example, the WP controller configures to perform an acquisition every 20 ms, while the field radiation detector is moved continuously at 3 mm/s. Alternatively, it performs an acquisition every 20 ms, wherein each acquisition is separated by a time break while the field radiation detector is moved from one position of measurement to another. The different (pre)determined WP times are computed in function of at least, the duration for moving the field radiation detector from one position to another, and the duration of the measurements of the dose with the field radiation detector 31.

In the automatic mode of the method, the QA controller 50 generates of a sequence of radiation beams comprising the duration of the emission of the radiation beams. This sequence is based on the measurements plan.

Once the sequence of positions in the motorised water phantom at different (pre)determined WP times and the sequence of radiation beams are established, the commissioning or QA verification may be performed automatically. For example, the method measures the dose rate for several positions in the X, Y plane, for several depths, Z, for several beam qualities and for several radiation fields one after the other, and checks the synchronism between the sequence of radiation beams and the sequence of measured scans.

FIGS. 4(*a*) to (*e*) illustrate examples of commissioning or QA verifications in which the predefined sequences of radiation beams and predefined sequences (measurements) are synchronous (a) or not (b) to (e) to each other. The first graph of each figure corresponds to the emission of radiation beams I(t) with respect to the time, t, according to the predefined sequence of radiation beams (B1, B2, . . . ). The second graph corresponds to the positions (or mean positions in continuous mode) P(t) of the field radiation detector with respect to the time, t, according to predefined sequence of positions in the motorised WP 3, at predefined WP times. The third and fourth graphs respectively correspond to the signals acquired by the field, D(t), and reference, R(t), radiation detector.

In step-by-step mode, a first radiation field F1 may be defined and a first radiation beam B1 may be emitted according to the predefined sequence of radiation beams. The field radiation detector 31 may be moved to a first position P11 according to the predefined sequence of positions, and a signal is acquired by the field D11 and reference R1 radiation detector. Then, the field radiation detector may be moved to a second position and a signal is acquired by the field D12 and reference R1 radiation detector. The sequence is repeated until all the position of the first radiation field F1 are covered. Several radiation fields may be tested.

In continuous mode, a first radiation field F1 may be defined and a first radiation beam B1 may be emitted according to the predefined sequence of radiation beams. The field radiation detector 31 is continuously moved along a predetermined track according to the predefined sequence of positions, and a signal is acquired during the movement. The graph D(t) thus represents the integrated value of the signals representative of the field radiation doses rate acquired during a given time. The signal representative of the flux rate acquired with the reference radiation detector is measured during the same given time. Several radiation fields may be tested.

An example of commissioning or QA verification may include:
- defining a size of the radiation field F1 (with a MLC, for example) according to the sequence of radiation beams, this operation is controlled by the RT controller;
- emitting a first radiation beam B1 with the RT device according to the sequence of radiation beams, this operation is controlled by the RT controller;
- moving the field radiation detector according to the sequence of positions (either sequentially or continuously), through the positions P11 . . . P1N covered by a scan, this operation is controlled by the WP controller;
- acquiring signal from field radiation detector with the WP controller, acquiring signal from reference radiation detector with the QA controller, transmitting these signals to the QA controller, computing the dose rate at positions P11 . . . P1N (with the WP or QA controller);
- stopping the emission of the radiation beam according to the sequence of radiation beams, this operation is controlled by the RT controller;
- checking that the sequence of positions and the sequence of radiation beams are synchronized, this check being performed by the QA controller and is based on the signal from field and reference radiation detectors.

Figure 2E:
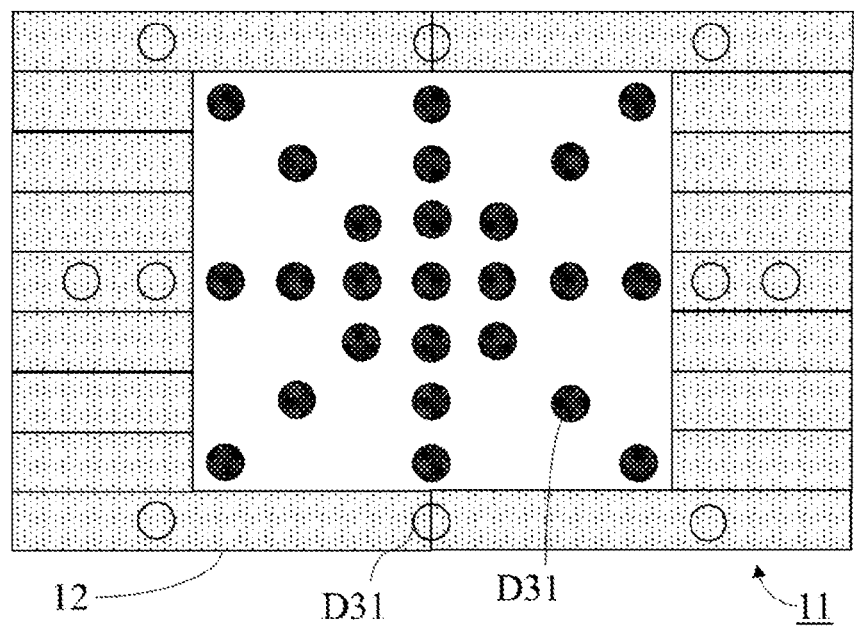

The positions of the predetermined sequence of positions are preferably chosen to cover a region representative of the whole radiation field F1 (for example, a configuration such as illustrated on FIG. 2(e)). Then, another field F2 is defined and the steps (b) to (f) are repeated for different positions for the radiation field F2, of the field radiation detector. Finally, the commissioning or QA verification is finished when all the points of all radiation fields Fj with j=1 to N and N is the number of radiation fields have been measured. The commissioning or QA verification according to the present disclosure is automated and, once started, is completely executed according to the Measurements plan. In case of detection of a non-synchronism, an error may be recorded and/or the procedure may be stopped.

The synchronism between the sequence of radiation beams and the sequence of positions is checked by the QA controller 5. The following methods are suitable for checking this synchronism:
- (A) determining the presence or the absence of detection of the radiation beam with the reference radiation detector;
- (B) comparing the value of the signal measured with the reference radiation detector with a size of a field defined in the Measurements plan;
- (C) if a log file is available, comparing the sequence of radiation beams and their characteristics with the content of a record of the RT device operational data.

The methods may be implemented alone or in combination. Other methods may be implemented.

FIG. 4 show examples of commissioning or QA verifications where the sequence of positions and the sequence of radiation beams are synchronized (a) or not synchronized ((b) to (e)). In this example, the procedure of commissioning or QA verification consists in delivering two fields, F1 and F2, F2 being smaller than F1. The sequence of radiation beams thus comprises the emission of two beams, B1 and B2. The RT device emits the first beam B1 between a time t1 and a time t2, and emits the second beam B2 between a time t3 and a time t4.

Figure 4A:
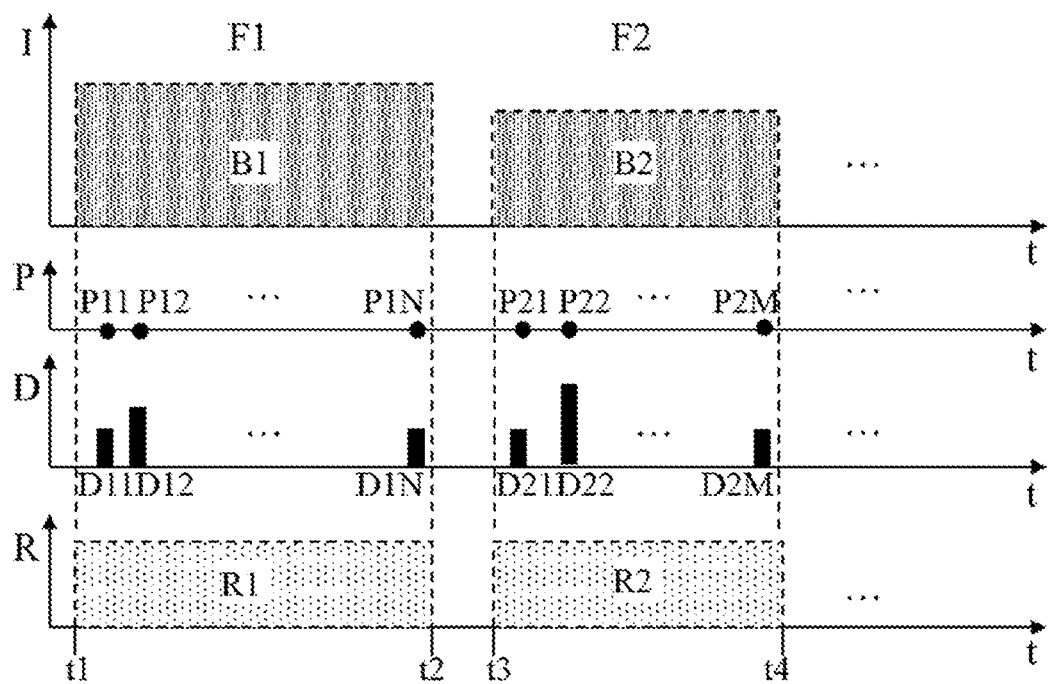
Figure 4B:
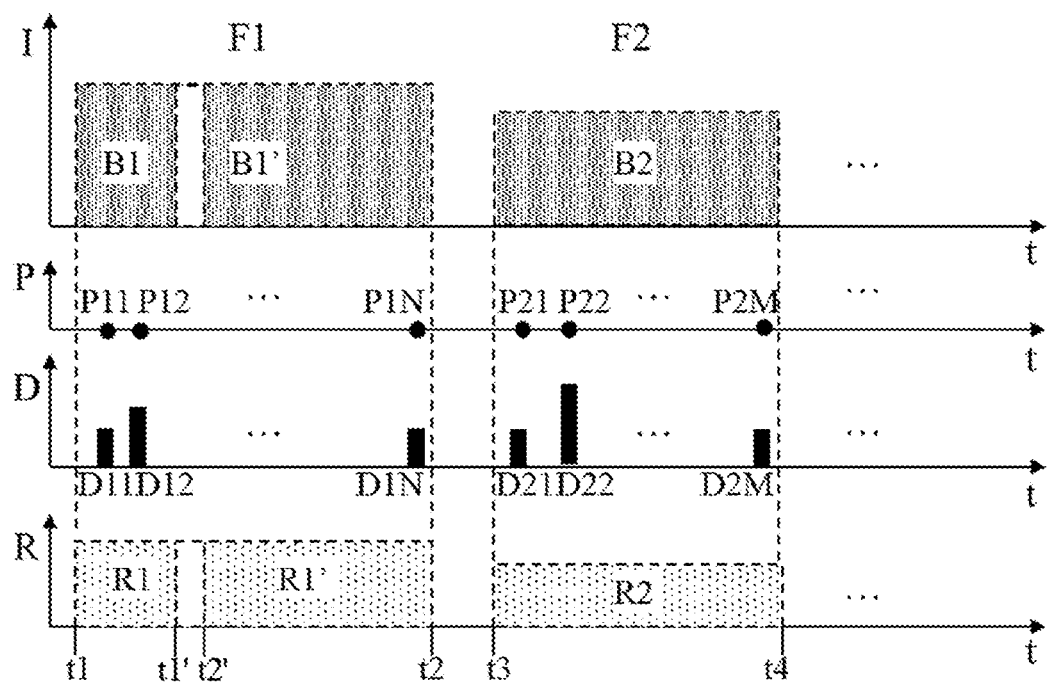

A first way to check the synchronism (method (A)) may be based on on/off transitions measured with the reference radiation detector. In the example of FIG. 4(a), when 4 on/off transitions, at t1 (on), t2 (off), t3 (on), and t4 (off) are recorded, it is considered that the sequence are synchronous. This first method does not ensure that the beam has been delivered during a sufficiently long time for performing the sequence of positions. FIG. 4(b) illustrates an example wherein the emission of the first radiation beam B1, B1' has been unexpectedly interrupted. The reference radiation detector thus records 6 on/off transitions. Based on these unexpected transitions, the QA controller may emit a warning message or interrupt the procedure.

A second way to check the synchronism (method (B)) may be based on the duration of the signal measured by the reference radiation detector. In the example, the reference radiation detector provides a (non-negligible) signal during a first time interval $dt1=t2'-t1$; and a second time interval $dt2=t4-t3$. This second method allows comparing the delivering time with the time of scan of the predefined sequence of positions. In the FIG. 4(d), the number of on/off transition is the one expected but the duration, $dt'=t2'-t1$, of the emission of the first radiation beam B1 is shorter than the duration planned, $dt1=t2-t1$. Based on this shorter duration, the QA controller may emit a warning message or interrupt the procedure.

The combination of the two methods ((A) and (B)) allows to check:
- if the beginning of the emission of a radiation beam according to the predefined sequence of radiation beams and the beginning of the scan according to the predefined sequence of positions are synchronous;
- if the number of on/off transitions is the one expected;
- if the duration of the emission of a radiation beam according to the predefined sequence of radiation beams is the one computed for allowing the scan according to the predefined sequence of positions.

Figure 4C:
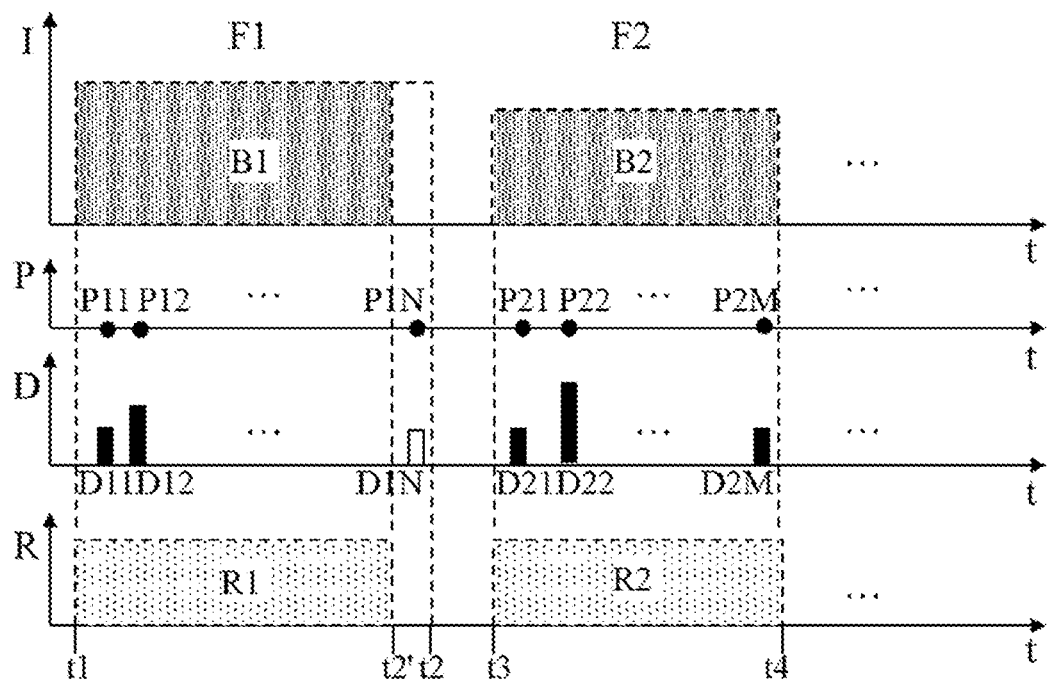
Figure 4D:
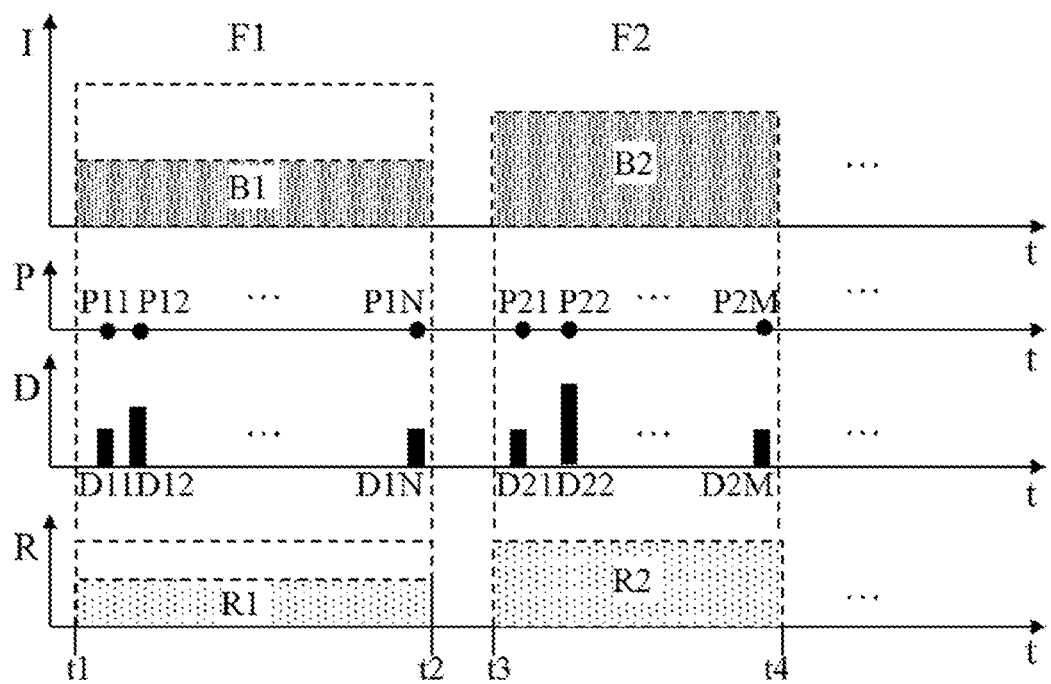

An alternative of the method (B) is based on the amplitude of the signal measured with the reference radiation detector. The amplitude of the signal is proportional to field size. For example, if the edge lengths (size) of field F1 are twice edge length (size) of field F2, the field will irradiate 4 times the area and the signal measured with the reference radiation detector for the field F1 is 4 times greater than the signal measured with the reference radiation detector for the field F2. The QA controller compares if the values of the signal measured with the reference radiation detector correspond to the one expected according to the predefined sequence of radiation beams. FIG. 4(c) illustrates an example wherein the number of on/off transitions and the duration of the emission of the first radiation beam are the ones expected. The amplitude of the signal produced by the first radiation beam B1, and measured with the reference radiation detector is, however, smaller than the one expected. Based on this smaller amplitude, the QA controller may emit a warning message or interrupt the procedure.

A third way to check the synchronism (method (C)) uses the information contained in a log file. For example, the log file comprises the number of MU delivered respectively for the field F1 and F2, the duration of the emission of the radiation beams, B1, B2, the size of the fields, F1, F2. If the emission of a radiation beam has been interrupted, the log file contains, in some embodiments, an indication of this interruption. The QA controller compares this information to the signals measured with the reference radiation detector and, optionally, to the signals measured with the field radiation detector to check the synchronism. The log file is often available after the delivery of the measurements plan and may only be used for a check after irradiation has completed.

Figure 4E:
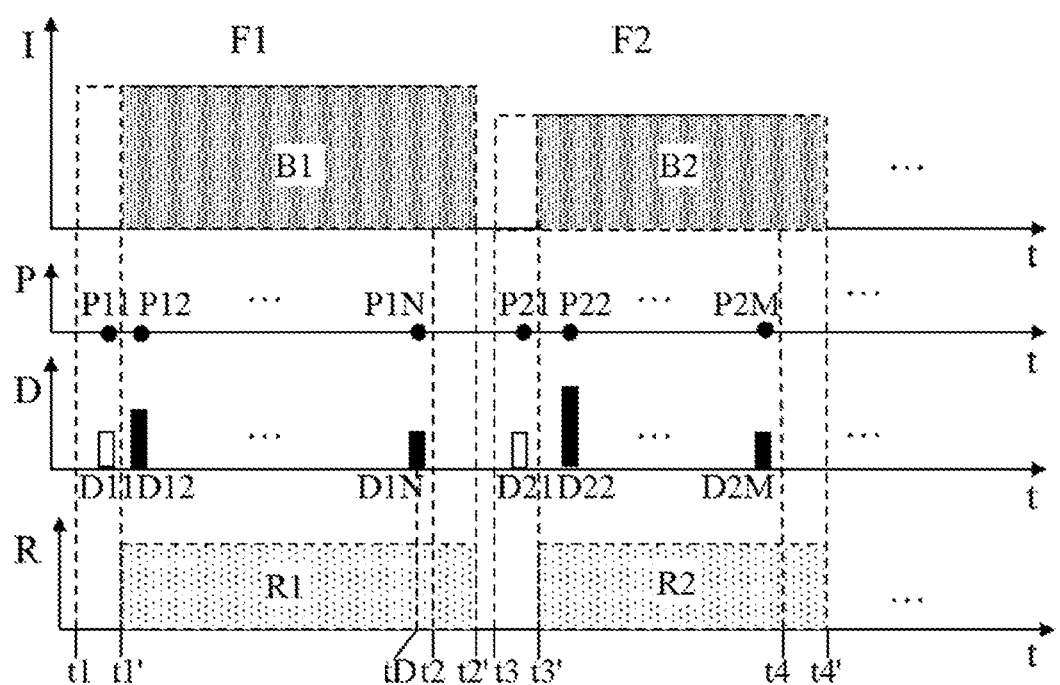

FIG. 4(e) shows an example wherein the combination of several methods may be required for checking the synchronism. In this example, the number of on/off transitions, the duration and amplitude of the emission of radiation beams are the ones expected, but the predefined sequence of radiation beams has been delayed with respect to the predefined sequence of positions. In this case, the QA controller should compare the time; t1', at which a signal has been measured with the reference radiation detector and time, t1, of the beginning of the scan of the predefined sequence of positions. Another possibility is to compare the time, tD, of the last signal measured with the field radiation detector, D1N, (tD=t2−Δt) of the first field, F1, with the time t2', of the end of the signal, R1, measured with the reference radiation detector. The delay between these two times, tD and t2' has to be smaller than or equal to a predetermined delay Δt. Otherwise, the QA controller may emit a warning message or interrupt the procedure. Alternatively or complementarily, the QA controller uses the log file to compare the timestamp of the emission of the radiation beam with the time of the signals measured with the field radiation detector.

The QA controller is preferably configured to implement several methods. For example, the first radiation beam, B1, associated with the first field, F1, generates a signal of amplitude, A1, measured with the reference radiation detector, and the second radiation beam, B2, associated with the second field, F2, generates a signal of amplitude, A2 different from A1, measured with the reference radiation detector. The first radiation beam may suffer from an accidental interruption. An unexpected on/off transition is thus recorded and the QA controller suspends the scan according to the predefined sequence of positions. When the beam is restarted, an on/off transition is recorded. The reference radiation detector measures an amplitude, A'. If the amplitude A' is equal to A1, the scan is resumed by the QA controller that concludes that the pause was an accidental break. A warning is preferably recorded. If the amplitude A' is equal to A2, the QA controller preferably interrupts the procedure.

The methods suitable for checking the synchronism between the sequence of radiation beams and the sequence of positions given above are illustrative examples. Other methods for checking this synchronism and based on the signals received from the field radiation detector and from the reference radiation detector, may be implemented by the one skilled in the art.

The apparatus according to the present disclosure enables optimization of commissioning or periodic QA verification of an RT device 1 by using the reference radiation detector 4 and the QA controller 50. The field radiation detector 31 automatically moves according to the predefined sequence of positions. The RT device emits radiation beams 2 according to the predefined sequence of radiation beams in the automatic mode, and according to operator input in the semi-automatic mode, and the QA controller 50 checks that these sequences are synchronously executed. The quality of the measurement is thus independent of the skill of the operator and the risk of human errors is greatly decreased.

The invention claimed is:

1. An apparatus for commissioning or performing a quality assurance (QA) verification of a radiation therapy (RT) device able to emit a radiation beam, and comprising a beam limiting device adapted for limiting the radiation beam to irradiate a field having at least one of a given field size and a given field shape, the apparatus comprising:
   a) a motorised water phantom (WP) comprising:
      a water tank;
      a field radiation detector configured for measuring a signal indicative of a field radiation dose rate of a radiation beam at a position in said water tank;
      a mechanical drive configured for moving said field radiation detector to a given position at a given speed in said water tank; and
      a WP controller configured for:
         instructing said mechanical drive to move the field radiation detector to said given position at said given speed;
         acquiring a dose rate from said field radiation detector;
   b) an RT controller configured for:
      obtaining operation parameters of one or more fields, each of the one or more fields comprising at least one of a field size or field shape, a beam energy, a dose rate, and a dose; and
      causing the RT device to emit a beam according to said operation parameters;
   c) a QA controller comprising:
      a memory for storing a measurements plan, said measurements plan comprising data defining a sequence of the one or more fields wherein each field comprises a set of scans, and each scan defines a path to be measured in the radiation beam;
      a communication interface for transferring data of said scans to said WP controller; and
      an acquisition interface for acquiring and storing the dose rate from said field radiation detector; and
   d) a reference radiation detector configured and positioned for intercepting said radiation beam and for measuring the dose rate of said radiation beam, wherein said reference radiation detector is substantially transparent to said radiation beam;
      wherein said QA controller comprises:
      an acquisition interface for acquiring and storing the dose rate from said reference radiation detector; and
      a processor configured for checking a synchronism between the dose rate from the field radiation detector and the dose rate from the reference radiation detector, and for checking a synchronism between a sequence of radiation beams and a sequence of positions by comparing the value of a signal measured with the reference radiation detector with a field size defined in the measurements plan.

2. The apparatus of claim 1, wherein:
   the QA controller further comprises a QA operator console configured for displaying the data of said sequence of the one or more fields, and
   the RT controller further comprises a RT operator console configured to receive data of a selected one of said one or more fields and start the beam.

3. The apparatus of claim 1, wherein the QA controller further comprises:
   a processor for producing a file containing data for the sequence of the one or more fields, and
   a communication interface for transferring said file to said RT controller, the RT controller comprising a communication interface for receiving said file and starting execution of the one or more fields contained therein.

4. The apparatus of claim 1, wherein:
   at least one of the field radiation detector comprises a first electrometer, the reference radiation detector comprises a second electrometer, and
at least one of the WP controller or the QA controller is respectively configured for automatically adjusting a gain of at least one of the first electrometer or the second electrometer as a function of a maximum dose rate of a field.

5. The apparatus according claim 1, wherein the field radiation detector is selected from a group consisting of a scintillating detector, a diode, a linear array of diodes, a 2D planar array of diodes, an ionisation chamber, a linear array of ionisation chambers, and a 2D planar array of ionisation chambers.

6. The apparatus of claim 1, wherein:
the reference radiation detector is an integral ionisation chamber,
said integral ionisation chamber is configured for intercepting at least 90% of a field region of the radiation beam, and
the field region is defined as a separation between a 50% dose level point on a beam profile and a penumbra around a central region.

7. The apparatus of claim 1, wherein:
the RT controller is configured for generating a log file comprising at least one of a count of monitor units (MU) emitted by the RT device, a presence or an absence of a beam limiting device, a presence or an absence of a multileaf collimator, or a sequence of records,
the sequence of records comprises at least one of a position of leaves of the multileaf collimator, an orientation of the radiation beam, one or more characteristic of the radiation beam, and
the QA controller is further configured to use the log file for checking the synchronism between a sequence of radiation beams and a sequence of scans.

8. The apparatus of claim 1, wherein the QA controller is configured for checking the synchronism between a sequence of radiation beams and a sequence of positions by performing at least one of the following steps:
a) determining a presence or an absence of detection of the radiation beam with the reference radiation detector; or
b) comparing the sequence of radiation beams and characteristics of the radiation beams with a content of a log file comprising records of RT device operational data.

9. A method for commissioning or performing a periodic quality assurance (QA) verification of a radiation therapy (RT) device using the apparatus according to claim 1, the method comprising:
a) obtaining the measurements plan comprising the sequence of the one or more fields, each field comprising the set of scans;
b) transferring said sequence of fields to the RT controller;
c) transferring the set of scans to the WP controller;
d) controlling, using the RT controller, the RT device for emitting said one or more fields;
e) instructing, using the QA controller, the WP controller to start moving the field radiation detector according to the scans, when the QA controller receives a signal from the reference radiation detector that a beam was started;
f) acquiring, using the QA controller, the measurements from the field radiation detector and from the reference radiation detector; and
g) checking, using the QA controller, the synchronism between the measurements acquired from the field radiation detector and the measurements acquired from the reference radiation detector.

10. The method according to claim 9, wherein:
step a) is performed by viewing the data of the one or more fields of the measurements plan displayed at an operator console of the QA controller; and
step b) is performed by entering the data of the one or more fields of the measurements plan to the RT controller by using an operator console of the RT controller.

11. The method according to claim 9, wherein:
step a) is performed by the QA controller producing a file containing the sequence of the one or more fields; and
step b) is performed by the QA controller providing said file to the RT controller.

12. The method according to claim 9, further comprising checking, using the QA controller, a synchronism between the sequence of the one or more fields and the set of scans, wherein the checking is determined according to at least one of:
a) a presence or an absence of detection of the radiation beam with the reference radiation detector;
b) the comparison of the value of the signal measured with the reference radiation detector with the field size defined in the measurements plan; or
c) a comparison of the sequence of radiation beams and characteristics of the radiation beams with a content of a log file comprising records of RT device operational data, wherein:
the RT controller is configured for generating a log file comprising at least one of a count of monitor units (MU) emitted by the RT device, a presence or an absence of a beam limiting device, a presence or an absence of a multileaf collimator, or a sequence of records,
the sequence of records comprises at least one of a position of leaves of the multileaf collimator, an orientation of the radiation beam, one or more characteristic of the radiation beam, and
the QA controller is further configured to use the log file for checking the synchronism between a sequence of radiation beams and a sequence of scans.

13. The method according to claim 9, further comprising emitting a warning notification, using the QA controller, if the sequence of radiation beams and the sequence of positions lose synchronism.

14. The method according to claim 9, further comprising one of:
temporary suspending the sequence of radiation beams or the sequence of positions; and
restarting the sequence of radiation beams and the sequence of positions from the beginning or from the last emission and movement that were synchronous.

15. The method according to claim 9, wherein:
the field radiation detector is selected from a group consisting of a scintillating detector, a diode, a linear array of diodes, a 2D planar array of diodes, an ionisation chamber, a linear array of ionisation chambers, and a 2D planar array of ionisation chambers, and
the method further comprises at least one of:
automatically adjusting a gain of a field electrometer as a function of a maximum dose rate of each beam of the sequence of radiation beams; or
automatically adjusting a gain of a reference electrometer as a function of a flux rate of each beam of the sequence of radiation beams.

16. A computer program comprising instructions which, when the program is executed by a computer, cause the computer to carry out the method of claim 9.

* * * * *